United States Patent [19]

Colombo

[11] 4,434,291

[45] Feb. 28, 1984

[54] MULTIFUNCTIONAL ADDITIVES FOR LUBRICANTS

[75] Inventor: Edilberto Colombo, Aicurzio, Italy

[73] Assignee: Agip Petroli S.p.A., Rome, Italy

[21] Appl. No.: 385,081

[22] Filed: Jun. 4, 1982

[30] Foreign Application Priority Data

Jun. 26, 1981 [IT] Italy ................................ 22583 A/81

[51] Int. Cl.$^3$ ................................................ C07F 9/65
[52] U.S. Cl. ................................ 548/116; 252/46.7; 548/117; 548/239; 548/347; 548/352
[58] Field of Search ............... 548/239, 347, 352, 116, 548/117

[56] References Cited

U.S. PATENT DOCUMENTS

| | | | |
|---|---|---|---|
| Re. 23,227 | 5/1950 | Blair et al. | 548/347 |
| 2,442,582 | 6/1948 | Bishop | 548/239 |
| 2,564,423 | 8/1951 | Barnum | 548/239 |
| 3,523,123 | 8/1970 | Wehrmeister | 548/347 |
| 3,920,567 | 11/1975 | Miller | 252/32.5 |
| 4,255,271 | 3/1981 | Horodysky et al. | 548/239 |

*Primary Examiner*—Richard Raymond
*Attorney, Agent, or Firm*—Hedman, Gibson, Costigan & Hoare

[57] ABSTRACT

A multifunctional ashless additive is described having antiwear and antioxidant properties and high antirust power, and is prepared by reacting a O,O'-dialkylthiophosphoric acid with a compound chosen from substituted 2-oxazolines and substituted imidazolines.

6 Claims, No Drawings

MULTIFUNCTIONAL ADDITIVES FOR LUBRICANTS

This invention relates to multifunctional additives of the so-called ashless type for lubricants, and methods for their preparation.

More particularly, the invention relates to the preparation of antiwear, antioxidant, anticorrosive and antirust additives soluble in mineral and/or synthetic oils and used for formulating internal combustion engine lubricants, transmission fluids and hydraulic fluids.

Metal salts of O,O-dialkyldithiophosphoric acids, especially zinc salts, have been universally used for many years as antioxidant and antiwear additives in engine oils and transmission fluids.

These metal salts have drawbacks due particularly to their high ash content, and this becomes increasingly less negligible due to the present tendency of subjecting the lubricant to increasingly severe service conditions.

In this respect, an increasingly arduous performance and increasingly lengthy operating times are required of the lubricant, these being mostly attained by means of increasing additive quantities, especially with regard to the inhibition of oxidation processes.

In the case of metal dithiophosphates, this tendency leads to an increase in the ash content of the lubricant.

It is well known that additives of high ash content can give rise to deleterious deposits on the lubricated surfaces, so considerably reducing the effectiveness of the lubricant to the point at which catastrophic wear occurs.

For this reason, ashless dithiophosphates, most of which are based on amino salts of O,O-dialkyldithiophosphoric acids, are becoming increasingly widely used.

The present invention therefore relates to dithiophosphates of ashless type, which thus have no drawback deriving from ash content.

In addition they have high antirust power, which together with their unaltered antioxidant and antiwear characteristics increases their range of application, while at the same time allowing formulation simplification.

The object of the present invention is therefore to provide a multifunctional ashless additive of antiwear and antioxidant properties comparable with those of zinc dialkyldithiophosphates, plus high antirust power.

The multifunctional additive can be prepared by reacting:

(a) a O,O'-dialkyldithiophosphoric acid of formula:

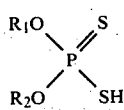

where
R$_1$ and R$_2$, which are the same or different, are hydrocarbon radicals, preferably alkyl, containing from 3 to 20 carbon atoms, with (b) a substituted 2-oxazoline of formula

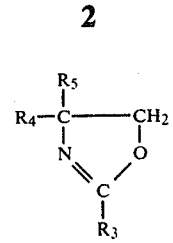

where
R$_3$ is a hydrocarbon group, particularly alkyl, containing from 1 to 30 carbon atoms, and R$_4$ and R$_5$, which are the same or different, can be either H atoms or hydrocarbon groups, preferably alkyl, containing from 1 to 5 carbon atoms, or methylol groups; or with (b') a substituted imidazoline of formula:

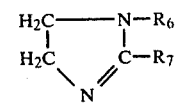

where
R$_6$ and R$_7$, which are the same or different, are saturated or unsaturated hydrocarbon groups, preferably alkyl, containing from 1 to 30 carbon atoms; the use of the product in which R$_6$ is H and R$_7$ is CH$_2$CH$_2$OH has been found particularly advantageous.

The oxazoline can be prepared by reacting an appropriate aminoalcohol with a carboxylic acid.

The aminoalcohol must be of the 2,2'-disubstituted 2-amino-1-alkanol type comprising 2 or 3 hydroxyl groups, and represented by the formula

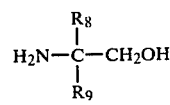

where the substituents R$_8$ and R$_9$ represent either an alkyl or a hydroxyalkyl group. The preferred product is one in which both the substituents are of hydroxyalkyl type, namely —(CH$_2$)$_n$OH where n is 1, 2 or 3.

The imidazoline can be prepared from 1,2 diaminoethane and carboxylic acid as described in U.S. Pat. No. 2,267,965. In both cases, isostearic acid is particularly preferred.

The multifunctional additive can be prepared either by treating the dithiophosphoric acid with a nitrogenated compound of the aforesaid type synthesised separately and at different times, or more simply by synthesising the acid in the presence of the neutralising nitrogenated substrate.

The adduct is formed with high yields, and can be prepared by adding at least 1 gram atom of nitrogen per mole of dithiophosphoric acid.

The neutralisation reaction can be carried out either with or without solvent, at a temperature of 0°–100° C., preferably at a temperature of 20° C. and in an inert atmosphere.

The reaction time, which can vary according to the nature of the substituents, does not exceed 4–5 hours.

The disappearance of the reactants and the formation of the adduct can be followed during the course of the neutralisation reaction by the normal chromatographic and/or spectroscopic means.

The following non-limiting examples serve to illustrate the preparation of the additives according to the invention.

EXAMPLE 1

The oxazolines used for neutralising the dithiophosphoric acid were prepared by reacting isostearic acid with the chosen aminoalcohol in the following manner:

The following were added to 282 g (1 mole) of isostearic acid in a four-neck glass reactor:

(a) in a first case, 121 g (1 mole) of 2-amino-2-hydroxymethyl-1,3-propanediol;

(b) in a second case, 105 g (1 mole) of 2-amino-2-methyl-1,3-propanediol;

(c) in a third case, 89 g (1 mole) of 2-amino-2-methyl-1-propanol.

The respective reaction mixtures were then raised to a temperature of 160°–170° C. until the scheduled water quantity had been collected.

EXAMPLE 2

130 g (1 mole) of 2-isooctyl alcohol were added at a temperature of 40°–60° C. over a period of 3 hours to 55 g of $P_2S_5$ (0.25 moles) in 150 ml of toluene. The temperature of the reaction mixture was then raised to 80°–90° C. and kept at this level for 5 hours until the $P_2S_5$ disappeared.

The filtered solution was ready for the subsequent neutralisation reaction.

EXAMPLE 3

21.2 g of 4-hydroxymethyl-2-isoheptadecenyl-oxazoline prepared as described in example 1 a were added to a solution of 21.6 g of diisooctyldithiophosphoric acid (0.06 moles) in 50 ml of toluene. The reaction mixture was kept stirred under an inert atmosphere for 3 hours at 20° C. The complete conversion of the reactants into the adduct was checked by thin layer chromatography using 60 $F_{254}$ silica gel as the stationary phase, and a toluene/methanol mixture in the ratio of 70:30 by weight as the eluent. The product obtained is homogeneous and soluble in mineral oils.

EXAMPLE 4

As in the preceding example, 20.2 g of 4,4'-bis(hydroxymethyl)-2-isoheptadecenyl-oxazoline prepared as described in example 1 b were added to a solution of 21.6 g of diisooctyldithiophosphoric acid (0.06 moles) in 50 ml of toluene. The neutralisation product, obtained with a yield exceeding 95% after 4 hours of mixing at 20° C. is homogeneous and in contrast to the initial oxazoline is soluble in mineral oils.

EXAMPLE 5

As in the latter two examples, 22.1 g of 4-methyl-2-isoheptadecenyl oxazoline prepared as in example 1 c were added to a solution of 21.6 g of diisooctyldithiophosphoric acid (0.06 moles) in 50 ml of toluene.

The reaction time at 20° C. was 2.5 hours. The product obtained is soluble in mineral oils.

EXAMPLE 6

26.1 g (0.08 moles) of commercial 1-hydroxyethyl-2-heptadecenyl imidazoline were added to a solution of 28 g of diisooctyldithiophosphoric acid (0.08 moles) in 50 ml of toluene.

In evaluating the additives according to the present invention, a zinc dithiophosphate prepared from the same dithiophosphoric acid used for the synthesis of the aforesaid compounds was used as the reference.

In this manner, high antirust power was observed in addition to the antiwear and antioxidant power typical of conventional metal dithiophosphates.

Antiwear power

In evaluating the antiwear power of the additives according to the present invention, a four-ball wear machine with steel balls was used, operating under the following conditions:

angular velocity: 126 rad/s, load: 40 daN, oil temperature: 75° C., test duration: 1 h.

Table 1 shows the results, expressed as wear diameter in mm, for the SN150 oil as such, for zinc diisooctyldithiophosphate and for the additives prepared and used according to the present invention. The additives for which the comparative evaluation of wear performance was made are present in SN150 at the same phosphorus concentration of 0.07%.

TABLE 1

| Additive | Wear diameter (mm) |
| --- | --- |
| SN 150 | 0.95 |
| Product of 3 | 0.44 |
| Product of 4 | 0.45 |
| Product of 5 | 0.40 |
| Product of 6 | 0.40 |
| 7 | 0.45 |

7 being zinc diisooctyldithiophosphate.

From the data given in the table it can be seen that the new ashless dithiophosphates substantially improve the lubricant behaviour with regard to wear in the same manner as zinc dithiophosphate.

Antioxidant power

One of the primary actions of metal dithiophosphates is known to be their antioxidant action.

In order to evaluate this property in the case of the described additives, an oxidation test was used in which air was bubbled through in the presence of copper and iron strips.

For this purpose, a copper strip and an iron strip were immersed in a test tube containing 50 g of a solution of the various additives under examination in SN450, all at the same phosphorus concentration of 0.07%.

The test tube was placed in a bath which was temperature controlled at 175° C., and an air stream was passed through the solution at a throughput of 50 Nl/h for 48 hours. The oil viscosity at 40° C. before and after the oxidation test was chosen as the quantity which indicated the antioxidant performance. The smaller the degree of thickening of the oil, the better the antioxidant performance of the additive.

TABLE 2

| Additive | Viscosity at 40° C. | |
| --- | --- | --- |
| | Before | After |
| --- | --- | --- |
| SN 150 | 30.15 | 40.78 |
| Product of 3 | 30.82 | 32.15 |

TABLE 2-continued

| Additive | Viscosity at 40° C. Before | Viscosity at 40° C. After |
| --- | --- | --- |
| Product of 4 | 30.93 | 31.03 |
| Product of 5 | 30.56 | 31.67 |
| Product of 6 | 31.46 | 32.72 |
| 7 | 30.62 | 31.29 |

As in the case of zinc dithiophosphate, the aforesaid ashless additives contain the viscosity of an oil subjected to an oxidation process, thus exercising the required antioxidant action.

Antirust power

Certain oxazoline and imidazoline derivatives are known to possess the characteristic of forming a film on metal surfaces, and for this reason they are used as antirust additives in lubricants. It was therefore obvious to check whether this behaviour was also present in their dithiophosphoric acid salts.

The antirust performance was evaluated in accordance with the ASTM D655 method.

300 ml of oil under examination are fed into a 400 ml beaker.

The beaker is then placed in a suitable bath which is temperature controlled at 60° C. A cylindrical steel test piece is then immersed in the oil under examination. 30 ml of distilled water are added under stirring 30 minutes after immersing the test piece.

The test is continued for 24 hours from the addition of the water.

TABLE 3

| Additive | Result |
| --- | --- |
| Product of 3 | pass |
| Product of 4 | pass |
| Product of 6 | pass |
| 7 | severe rusting |

This characteristic together with the absence of ash differentiates them from conventional dithiophosphates, so making them more versatile.

By this means, dithiophosphates are given an additional performance characteristic which increases their functionality and widens their application, while at the same time allowing simplification and saving in the formulation of the final oils.

I claim:

1. A multifunctional additive for lubricants with antiwear, antioxidant and high antirust power, which is prepared by reacting a O,O'-dialkyldithiophosphoric acid of the formula

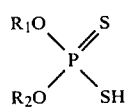

where $R_1$ and $R_2$, which can be the same or different, are alkyl radicals containing from 3 to 20 carbon atoms, with a nitrogenated derivative chosen from:

(a) a substituted 2-oxazoline of the formula

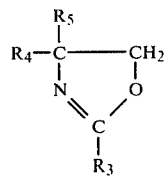

in which $R_3$ is an alkyl group containing from 1 to 30 carbon atoms, and $R_4$ and $R_5$, which can be equal or different, can be hydrogen or an alkyl group containing from 1 to 5 carbon atoms, and (b) a substituted imidazoline of the formula

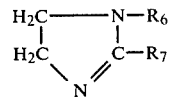

where $R_6$ and $R_7$, which can be the same or different and are alkyl groups containing from 1 to 30 carbon atoms.

2. A multifunctional additive for lubricants prepared by the reaction as claimed in claim 1, when said reaction takes place at a temperature of between 0° and 100° C.

3. A multifunctional additive for lubricants with antiwear, antioxidant, and antirust properties which is prepared by reacting an O,O'-dialkyldithiophosphoric acid of the formula:

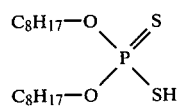

with a 2-oxazoline compound selected from compounds of the formula:

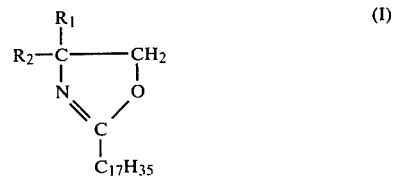

wherein $R_1$ and $R_2$ are the same or different and are selected from the group consisting of methyl and hydroxymethyl; or an imidazoline of the formula:

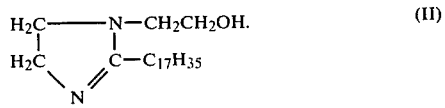

4. A multifunctional additive as defined in claim 3 wherein one of the reactants is a 2-oxazoline wherein $R_1$ and $R_2$ are both methyl.

5. A multifunctional additive as defined in claim 3 wherein one of the reactants is a 2-oxazoline wherein $R_1$ and $R_2$ are both hydroxymethyl.

6. A multifunctional additive as defined in claim 3 wherein one of the reactants is the imidazoline compound.

* * * * *